(12) United States Patent
Stridde et al.

(10) Patent No.: US 7,297,660 B2
(45) Date of Patent: Nov. 20, 2007

(54) ALKYLENE CARBONATE ADJUVANTS

(75) Inventors: Howard M. Stridde, Georgetown, TX (US); Curtis M. Elsik, Austin, TX (US); James R. Machac, Jr., The Woodlands, TX (US); Christopher J. Whewell, Georgetown, TX (US)

(73) Assignee: Huntsman Petrochemical Corporation, The Woodlands, TX (US)

( * ) Notice: Subject to any disclaimer, the term of this patent is extended or adjusted under 35 U.S.C. 154(b) by 184 days.

(21) Appl. No.: 10/471,783

(22) PCT Filed: Mar. 26, 2002

(86) PCT No.: PCT/US02/09224

§ 371 (c)(1),
(2), (4) Date: Feb. 2, 2004

(87) PCT Pub. No.: WO02/078441

PCT Pub. Date: Oct. 10, 2002

(65) Prior Publication Data

US 2004/0106523 A1 Jun. 3, 2004

Related U.S. Application Data

(60) Provisional application No. 60/279,487, filed on Mar. 28, 2001.

(51) Int. Cl.
*A01N 57/18* (2006.01)
*A01N 25/00* (2006.01)
*A01N 25/02* (2006.01)

(52) U.S. Cl. .............. 504/206; 504/116.1; 504/362

(58) Field of Classification Search ........... 504/206, 504/362, 307; 514/772, 975
See application file for complete search history.

(56) References Cited

U.S. PATENT DOCUMENTS 3,576,834 A 4/1971 Buchanen ............... 558/7
3,924,004 A 12/1975 Chang et al. ............ 514/772
3,934,005 A 1/1976 Albert .................... 514/477
4,155,971 A 5/1979 Wysong .................. 260/204
4,198,427 A 4/1980 Buchanan ................ 424/298
4,282,209 A 8/1981 Tocker .................... 424/81
4,481,215 A 11/1984 Tocker .................... 424/298
5,071,463 A 12/1991 Narayanan et al. ...... 504/116
5,156,666 A 10/1992 Narayanan et al. ...... 504/116
5,176,736 A 1/1993 Narayanan et al. ...... 504/116
5,200,421 A 4/1993 Ludwig et al. .......... 514/383
5,250,499 A 10/1993 Narayanan et al. ...... 504/116
5,283,229 A 2/1994 Narayanan et al. ...... 504/116
5,354,726 A 10/1994 Narayanan et al. ...... 504/116
5,389,300 A 2/1995 Schmitt et al. .......... 252/380
5,526,607 A 6/1996 Roesch et al. ........... 47/65.7
5,633,099 A * 5/1997 Yokoyama et al. ...... 429/332
5,677,307 A 10/1997 Gesing et al. ........... 514/383
5,843,978 A 12/1998 Wernthaler et al. ..... 514/404
5,874,025 A 2/1999 Heuer et al. ............ 252/383
6,503,891 B1 1/2003 Marquis et al. ......... 514/95

OTHER PUBLICATIONS

Ernest G. Jaworski, J. Agr. Food Chem., 1972, 20 (6), 1195-1198.*
Monsanto Company, MSDS Roundup Weed & Grass Killer Super Concentrate, Jul. 26, 2000.*
J. A. Ivany, Can. J. Plant Sci., 1988, 68, 1095-1101.*
Federal Register; vol. 63, No. 250, pp. 71920-71924; Dec. 30, 1998 PF-850;FRL-6050-1.

* cited by examiner

*Primary Examiner*—Johann R. Richter
*Assistant Examiner*—Nathan W. Schlientz
(74) *Attorney, Agent, or Firm*—Ron D. Brown; Edward D. Korompai (57) ABSTRACT

Provided herein are compositions of matter which contain an agriculturally-active material in combination with an agricultural adjuvant and at least one alkylene carbonate. The presence of an alkylene carbonate in such formulations increases the efficacy of herbicides and pesticides used in controlling unwanted foliage and insects in commercial agriculture.

10 Claims, 4 Drawing Sheets

Figure 1 - Velvetleaf Control with Alkylene Carbonates

Figure 2 - Velvetleaf Control with Alkylene Carbonates and AMS

Figure 3 - Lambsquarters Control with Alkylene Carbonates

Figure 4 - Lambsquarters Control with Alkylene Carbonates and AMS

ALKYLENE CARBONATE ADJUVANTS

This application claims priority to U.S. provisional patent application Ser. No. 60/279,487 which was filed on Mar. 28, 2001 and which is currently still pending.

This application claims priority to International Application Number PCT/US02/09224, which was filed on Mar. 26, 2002.

TECHNICAL FIELD

This invention relates generally to compositions which are useful in commercial agriculture. More particularly, the invention relates to the inclusion of alkylene carbonates in agricultural formulations, which formulations also contain at least one surfactant and at least one agriculturally-active material.

BACKGROUND OF THE INVENTION

Herbicide compositions are often characterized according to both the identity of the active ingredient which they contain, and by the mode by which the active ingredient causes vegetation necrosis. Generally, most herbicides cause vegetation necrosis by interfering with one or more vital biological processes essential to the vegetation's survival. Yet, before the active ingredient of a herbicide can interfere with such biological processes, the active ingredient must somehow be absorbed into the vegetation. Unfortunately, this absorption is often hindered by the chemical nature of the active ingredient. Accordingly, in addition to active ingredients, most herbicide compositions also include other components, commonly termed adjuvants, that enhance the performance and absorption of the active ingredient.

Various types of adjuvants useful as components of formulations useful in agriculture are known in the art. However, the literature appears to lack any reference to the use of alkylene carbonates as adjuvants. While alkylene carbonates have been known and available in commercial quantities for over fifty years, they have only recently found use in some limited chemical systems as solvents. Alkylene carbonates have many characteristics that make them excellent solvents. For example, they are environmentally-friendly, biodegradable, and have a relatively low VOC rating. Further, the polarity of a blend containing an alkylene carbonate solvent may be custom-tailored by formulating the blend with other alkylene carbonates. Alkylene carbonates also have a low toxicity, high boiling point and high flash points, which taken together means that they may be generally regarded as being safe solvent systems.

One aspect of the present invention is directed toward the use of alkylene carbonate as adjuvants in agriculturally useful formulations. In another aspect the present invention is directed at compositions of matter useful in agriculture which comprise alkylene carbonates. Another aspect of the present invention is directed at methods of controlling unwanted vegetation or pests using such compositions. The inclusion of alkylene carbonates in agriculturally useful compositions improves the bioefficacy of such compositions.

BRIEF SUMMARY OF THE INVENTION

The present invention provides compositions useful in commercial agriculture comprising: a) an alkylene carbonate; b) an agriculturally-active material; and c) an agricultural adjuvant, wherein the alkylene carbonate is present in any amount between about 3% and 75% by weight based upon the total weight of said composition. The alkylene carbonate used as a component of a composition according to the invention is represented by the structure:

in which each of $R_1$ and $R_2$ may be independently a hydrogen, hydroxymethyl, $C_1$ though $C_{18}$ alkyl, including straight chain or branched alkyls; and aryl or alkylaryl groups, in which the benzene ring is substituted or unsubstituted with $C_1$ though $C_{18}$ alkyl groups.

DETAILED DESCRIPTION

Alkylene carbonates are cyclic esters of carbonic acid. The simplest alkylene carbonate is ethylene carbonate (EC), followed by propylene carbonate (PC) and 1,2-butylene carbonate (BC). Both PC and BC are liquids at room temperature. Alkylene carbonates may be produced by a number of processes, including the reaction of a glycol with phosgene, transesterification of a glycol with a diethyl carbonate, or by the reaction of the corresponding 1,2-epoxide with carbon dioxide in the presence of a catalyst, as such methods are known in the art. Table 1 shows the chemical and physical properties of JEFFSOL® brand EC, PC, and BC.

TABLE 1

Physical Properties of JEFFSOL ® Brand Alkylene Carbonates[1]

| Property | EC | PC | BC |
|---|---|---|---|
| Molecular Wt. (g/mole) | 88.06 | 102.09 | 116.12 |
| Boiling Point (° C.) | 248 | 242 | 251 |
| Freezing Point (° C.) | — | −49 | < −45 |
| Melting Point (° C.) | 36.4 | — | — |
| Flash Point (° F., PMCC) | 320 | 275 | 275 |
| Evaporation Rate (25° C., n-BuAc = 1.00) | <.005 | <.005 | <.005 |
| Density (g/ml, 25° C.) | 1.338* | 1.200 | 1.141 |
| Density (g/ml, 40° C.) | 1.321 | 1.183 | 1.127 |
| Molar Volume (ml/g mole, 25° C.) | 65.8 | 85.1 | 101.8 |
| Viscosity (cp, 25° C.) | 2.56* | 2.50 | 3.15 |
| Viscosity (cp, 40° C.) | 1.95 | 1.86 | 2.24 |
| CAS registry number | 96-49-1 | 108-32-7 | 4437-85-8 |

TABLE 1-continued

Physical Properties of JEFFSOL ® Brand Alkylene Carbonates[1]

| Property | EC | PC | BC |
|---|---|---|---|
| Volatile Organic Content (ASTM D-2369) | 34 | 28 | 18 |

[1]commercially available from Huntsman Petrochemical Corporation, The Woodlands, Texas.
*supercooled The Hansen Solubility Parameters, dipole moment, and surface tension data of JEFFSOL® brand EC, PC, and BC are shown in Table 2.

TABLE 2

Solubility Characteristics of JEFFSOL ® Brand Alkylene Carbonates

| Property | EC | PC | BC |
|---|---|---|---|
| Hansen Sol Par, total ($cal^{1/2}$ $cm^{-3/2}$) | 14.5 | 13.3 | 10.0 |
| Hansen Sol Par, dispersive ($cal^{1/2}$ $cm^{-3/2}$) | 9.5 | 9.8 | 8.3 |
| Hansen Sol Par, polar ($cal^{1/2}$ $cm^{-3/2}$) | 10.6 | 8.8 | 3.0 |
| Hansen Sol Par, hydrogen bonding ($cal^{1/2}$ $cm^{-3/2}$) | 2.5 | 2.0 | 4.8 |
| Dipole Moment (Debyes, 40° C.) | 4.80 | 4.98 | 5.28 |
| Surface Tension (dynes/cm, 25° C.) | 44.0* | 40.9 | 38.1 |
| Surface Tension (dynes/cm, 40° C.) | 42.2 | 39.6 | 37.0 |

*supercooled
n.a. = not available

Propylene carbonate and butylene carbonate also have a relatively low toxicity towards mammals. For example, the $LD_{50}$ in rabbits for undiluted PC is>20 mL/kg. Propylene carbonate was found to be non-toxic by inhalation to dogs and guinea pigs in a 21-day test. Propylene carbonate has been found to be Ames negative, and negative for genotoxicity in the Rat Hepatocyte Primary Culture/DNA Repair Test. Neat propylene carbonate has been found to cause moderate skin irritation, whereas cosmetic products containing in excess of 20% PC were essentially non-sensitizing. Beyer, Karl H., Jr., Bergfels, Wilmer F., Benndt, W m. D., Carlton, W m. H., Hoffmann, Deitrich K., Schroeter, Arnold L., and Shank, Ronald C., J. Am. Col. Tox. 6 (1), 23-51, 1987).

In addition, propylene carbonate is very readily biodegradable according to criteria promulgated by the European Union. Values of up to 90% of the Theoretical Oxygen Demand (ThOD) are obtained after 15 days at concentrations which may be typically observed in waste water treatment plants, and higher concentrations as well (250-2500 mg/L). These study results imply a very low bacterial toxicity. Propylene carbonate also did not show adverse effects during a 7 day test at 300 ppm on activated sludge bacteria taken from a wastewater treatment plant. Kayser, Gernot, Koch, Michael, Erlmann, Wolfgang, and Ruck, W.: Test Procedures for the Degradability and Bacterial Toxicity of Chlorinated Hydrocarbon Replacements [Testverfahren für Abbaubarkeit und Bakterientoxizität von CKW-Ersatzstoffen].

The adjuvants of the present invention may comprise any number of alkylene carbonates and mixtures thereof. Preferably, the adjuvants comprise a blend of propylene carbonate and butylene carbonate. The particular amount of propylene carbonate and butylene carbonate in the blend will depend on a variety of factors, including the nature of the surfactant used in conjunction with the blend, the nature of the herbicidal active ingredient used in conjunction with the blend, the proposed mode of application of the herbicidal composition, etc.

The adjuvants of the present invention may be used in conjunction with any number of surfactants, including, but not limited to, nonionic surfactants, anionic surfactants, cationic surfactants, and amphoteric surfactants. Preferably, the adjuvants of the present invention are used in conjunction with nonionic surfactants. More preferably, the adjuvants of the present invention are used in conjunction with alkyl phenol ethoxylates or branched alcohol ethoxylates.

Agriculturally-Active Materials

As used in this specification and the appended claims, the words "agriculturally-active material" means any chemical substance that: 1) when applied to a given foliage that is generally regarded as undesirable adversely affects the longevity and/or reproductive capability of such foliage; or 2) when applied to the vicinity where insects dwell adversely affects the longevity and/or reproductive capability of such insects; or 3) is regarded by those skilled in the art as possessing pesticidal (including either insecticidal or herbicidal) properties. Included within this definition are pesticides, which include both herbicides and insecticides, including without limitation those particular chemical materials such as: 2,4,5-T, Acephate, Acetamiprid, Acrinathrin, Aldicarb, Amitraz, Amitrole, Arsenic and its compounds, Bendiocarb, Benfuresate, Bensulfuron methyl, Bentazone, BHC, 2,4-D Bitertanol, Butamifos, Butylate, Cadusafos, Captafol(Difolatan), Captan, Carbaryl, Chinomethionat, Chlorfenvinphos, Chlorfluazuron, Chlorimuron ethyl, Chlormequat, Chlorobenzilate, Chlorpropham, Chlorpyrifos, Cinmethylin, Clofentezine, Copper terephthalate trihydrate, Cyanide compounds, Cyfluthrin, Cyhalothlin, Cyhexatin, Cypermethrin, Cyproconazole, Cyromazine, Daminozide, DCIP, DDT(including DDD,DDE), Deltamethrin, Demeton, Diazinon, Dicamba, Dichlofluanid, Dichlorvos, Diclomezine, Dicofol(Kelthane), Dieldrin(including Aldrin), Diethofencarb, Difenoconazole, Difenzoquat, Diflubenzuron, Dimethipin, Dimethoate, Dimethylvinphos, Edifenphos, Endrin, EPN, EPTC, Esprocarb, Ethiofencarb, Ethofenprox, Ethoprophos, Ethoxyquin, Etobenzanide, Etrimfos, Fenarimol, Fenbutatin oxide, Fenitrothion, Fenobucarb, Fenpyroximate, Fensulfothion, Fenthion, Fenvalerate, Flucythrinate, Flufenoxuron, Fluoroimide, Flusilazole, Flusulfamide, Flutolanil, Fluvalinate, Fosetyl, Fosthiazate, Glufosinate, Glyphosate, Guthion, Halfenprox, Heptachlor(including Heptachlor epoxide), Hexaflumuron, Hexythiazox, Imazalil, Imazosulfuron, Imibenconazole, Iminoctadine, Inabenfide, Inorganic bromide, Iprodione, Isophenphos, Isoprocarb, Lead & its compounds, Lenacil, Malathion, Maleic hydrazide, MCPA (including Phenothiol), Mepanipyrim, Mephenacet, Mepronil, Methamidophos, Methiocarb, Methoprene, Methoxychlor, Metolachlor, Metribuzin, Mirex, Myclobutanil, Nitenpyram, Oxamyl, Paclobutrazol, Parathion, Parathion-methyl, Pencycuron, Pendimethalin, Permethrin, Phenthoate, Phosalone (Rubitox), Phoxim, Picloram, Pirimicarb, Pirimiphos-methyl, Pretilachlor, Prohexadione, Propamocarb, Propiconazole, Prothiofos, Pyraclofos, Pyrazoxyfen, Pyrethrins, Pyridaben, Pyridate, Pyrifenox, Pyrimidifen, Pyriproxyfen, Quinalphos, Quinclorac, Sethoxydim, Silafluofen, Tebuconazole, Tebufenozide, Tebufenpyrad, Tecloftalam, Tefluthrin, Terbufos, Thenylchlor, Thiobencarb, Thiometon, Tralomethrin, Triadimenol, Tribenuron methyl, Trichlamide, Trichlorfon, Triclofos-methyl, Tricyclazole, Triflumizole, and Vamidothion.

Agricultural Adjuvants

Adjuvants are chemical materials which are often employed as a component of a mixture which also contains an agriculturally active material, and which adjuvants are designed to perform specific functions, including wetting, spreading, sticking, reducing evaporation, reducing volatilization, buffering, emulsifying, dispersing, reducing spray drift, and reducing foaming. No single adjuvant can perform all these functions, but different compatible adjuvants often can be combined to perform multiple functions simultaneously; thus, adjuvants are a diverse group of chemical materials. Within the meaning of the term "Adjuvants" is included any substance added to a spray tank to modify a pesticide's performance, the physical properties of the spray mixture, or both.

Spray application is perhaps the weakest link in the chain of events a pesticide follows through its development process. Some researchers claim that up to 70 percent of the effectiveness of a pesticide depends on the effectiveness of the spray application. Selection of a proper adjuvant may reduce or even eliminate spray application problems associated with pesticide stability, solubility, incompatibility, suspension, foaming, drift, evaporation, volatilization, degradation, adherence, penetration, surface tension, and coverage, thereby improving overall pesticide efficiency and efficacy.

Surfactant adjuvants physically alter the surface tension of a spray droplet. For a pesticide to perform its function properly, a spray droplet must be able to wet the foliage and spread out evenly over a leaf. Surfactants enlarge the area of pesticide coverage, thereby increasing the plant or pest exposure to the chemical. Without proper wetting and spreading, spray droplets often run off or fail to adequately cover these surfaces. Such materials enhance the absorbing, emulsifying, dispersing, spreading, sticking, wetting or penetrating properties of pesticides. Surfactants are most often used with herbicides to help a pesticide spread over and penetrate the waxy outer layer of a leaf or to penetrate through the small hairs present on a leaf surface.

While surfactant adjuvants may be anionic, cationic, or nonionic, the nonionic surfactants are in most common usage. The "multi-purpose" nonionic surfactants are composed of alcohols and fatty acids, have no electrical charge and are compatible with most pesticides. Certain other surfactants may be cationic (+charge) or anionic (−charge) and are specialty adjuvants that are used in certain situations and with certain products. Anionic surfactants are mostly used with acids or salts, and are more specialized and used as dispersants and compatibility agents. Cationic surfactants are used less frequently but one group, the ethoxylated fatty amines, sometimes are used with the herbicide glyphosate.

Silicone-based surfactants are increasing in popularity due to their superior spreading ability. Some of these surfactants are a blend of nonionic surfactants (NIS) and silicone while others are entirely a silicone. The combination of a NIS and a silicone surfactant can increase absorption into a plant so that the time between application and rainfall can be shortened. There are generally two types of organosilicone surfactants: the polyether-silicones that are soluble in water and the alkyl-silicones that are soluble in oil. Unlike polyether-silicone types, alkyl-silicone surfactants work well with oil-based sprays, such as dormant and summer oil sprays used in insect control. Alkyl-silicone-enhanced oil sprays can maximize insecticidal activity and even allow significantly lower pesticide use rates that reduce residue levels on crops.

Sticker adjuvants increase the adhesion of solid particles to target surfaces. These adjuvants can decrease the amount of pesticide that washes off during irrigation or rain. Stickers also can reduce evaporation of the pesticide and some slow ultraviolet (UV) degradation of pesticides. Many adjuvants are formulated as spreader-stickers to make a general purpose product that includes a wetting agent and an adhesive.

Extender adjuvants function like sticker surfactants by retaining pesticides longer on the target area, slowing volatilization, and inhibiting UV degradation.

Plant penetrant surfactants have a molecular configuration that enhances penetration of some pesticides into plants. A surfactant of this type may increase penetration of a pesticide on one species of plant but not another. Systemic herbicides, auxin-type herbicides, and some translocatable fungicides can have their activity increased as a result of enhanced penetration.

Compatibility agent adjuvants are especially useful when pesticides are combined with liquid fertilizers or other pesticides, particularly when the combinations are physically or chemically incompatible, such as in cases when clumps and/or uneven distribution occurs in the spray tank. A compatibility agent may eliminate problems associated with such situations.

Buffers or pH modifier adjuvants are generally employed to prevent problems associated with alkaline hydrolysis of pesticides that are encountered when the pH of a pesticide exceeds about 7.0 by stabilizing the pH at a relatively constant level. Extreme pH levels in the spray mixture can cause some pesticides to break down prematurely. This is particularly true for the organophosphate insecticides but some herbicides can break down into inactive compounds in a matter of hours or minutes in alkaline situations (pH>7). For example, the insecticide Cygon (dimethoate) loses 50 percent of its pest control power in just 48 minutes when mixed in water of pH 9. At a pH of 6, however, it takes 12 hours for degradation to progress to that extent. On the other hand, sulfonyl urea (SU) herbicides tend to break down more rapidly where the pH is below 7. At low pHs, the herbicide 2,4-D is an uncharged molecule. At higher pH, 2,4-D tends to become more anionic or negatively charged which can affect its movement in the environment. Leaf coatings often have a high pH that can contribute to poor performance with certain herbicides. The use of a buffering or acidifying adjuvant can stabilize or lower the pH of a spray solution thereby improving the stability of the pesticide being used.

Mineral control adjuvants are used to mask the problems associated with water hardness minerals in spray water which can diminish the effectiveness of many pesticides. Mineral ions such as calcium, magnesium, salts and carbonates are commonly found in hard water. These ions can bind with the active ingredients of some pesticides, especially the salt-formulation herbicides such as Roundup™ (glyphosate), Poast™ (sethoxydim), Pursuit™ (imazethapyr), and Liberty™ (glufosinate) resulting in poor weed control. The use of water-conditioning adjuvants gives hard water minerals something to bind with other than the herbicide. In addition, some ammonium sulfate-based adjuvants can be used to offset hard water problems. The electrolytes ammonium sulfate, ammonium nitrate, and urea ammonium nitrate are often used in this regard.

Drift retardant adjuvants improve on-target placement of pesticide spray by increasing the average droplet size, since drift is a function of droplet size with drops with diameters of 100 microns or less tending to drift away from targeted areas.

Defoaming agent adjuvants are used to control the foam or frothy head often present in some spray tanks that results from the surfactant used and the type of spray tank agitation system can often can be reduced or eliminated by adding a small amount of foam inhibitor.

Thickener adjuvants increase the viscosity of spray mixtures which afford control over drift or slow evaporation after the spray has been deposited on the target area.

Oil-based adjuvants have been gaining in popularity especially for the control of grassy weeds. There are three types of oil-based adjuvants: crop oils, crop oil concentrates (COC) and the vegetable oils. Crop Oil adjuvants are derivative of paraffin-based petroleum oil. Crop oils are generally 95-98% oil with 1 to 2% surfactant/emulsifier. Crop oils promote the penetration of a pesticide spray either through a waxy plant cuticle or through the tough chitinous shell of insects. Crop oils may also be important in helping solubilize less water-soluble herbicides such as Poast™ (sethoxydim), Fusilade™ (fluaziprop-butyl) and atrazine. Traditional crop oils are more commonly used in insect and disease control than with herbicides. Crop oil concentrates (COC) are a blend of crop oils (80-85%) and the nonionic surfactants (15-20%.). The purpose of the nonionic surfactant in this mixture is to emulsify the oil in the spray solution and lower the surface tension of the overall spray solution. Vegetable oils work best when their lipophilic characteristics are enhanced, and one common method of achieving this is by esterification of common seed oils such as rapeseed, soybean, and cotton. The methylated seed oils (MSO) are comparable in performance to the crop oil concentrates, in that they increase penetration of the pesticide. In addition, silicone-based MSOs are also available that take advantage of the spreading ability of the silicones and the penetrating characteristics of the MSOs.

The special purpose or utility adjuvants are used to offset or correct certain conditions associated with mixing and application such as impurities in the spray solution, extreme pH levels, drift, and compatibility problems between pesticides and liquid fertilizers. These adjuvants include acidifiers, buffering agents, water conditioners, anti-foaming agents, compatibility agents, and drift control agents.

Solvent adjuvants are organic solvents which may be added to a formulation to increase or otherwise modify the solubility of the other components of the formulation. Common solvents useful as solvent adjuvants include without limitation aromatic solvents, polycyclic aromatic solvents, aliphatic solvents, mineral oils, vegetable oils, alkylester solvents, mineral spirits, petroleum distillates, acetate esters, crop oils, chlorinated hydrocarbons, naphthas, N-alkylpyrollidones, paraffinic solvents, seed oils, alkylated seed oils, citrus oils and alcohols.

Fertilizer-based adjuvants, particularly nitrogen-based liquid fertilizers, have been frequently added to spray solutions to increase herbicide activity. Research has shown that the addition of ammonium sulfate to spray mixtures enhances herbicidal activity on a number of hard-to-kill broadleaf weeds. Fertilizers containing ammonium nitrogen have increased the effectiveness of the certain polar, weak acid herbicides such as Accent™ (nicosulfuron), Banvel™ (dicamba), Blazer™ (acifluorfen-sodium), Roundup™ (glyphosate), Basagran™ (bentazon), Poast™ (sethoxydim), Pursuit™ (imazethapyr), and 2,4-D amine. Early fertilizer-based adjuvants consisted of dry (spray-grade) ammonium sulfate (AMS) at 17 lbs per 100 gallons of spray volume (2%). Studies of these adjuvants has shown that Roundup™ (glyphosate) uptake was most pronounced when spray water contained relatively large quantities of certain hard water ions, such as calcium, sodium, and magnesium. It is thought that the ions in the fertilizer tied up the hard water ions thereby enhancing herbicidal action.

Thus, the words "agricultural adjuvant" when used in this specification and the appended claims means any material recognized by those skilled in the art of pesticides to be useful as an adjuvant material in connection with the formulation and/or use of a pesticide, and include all materials falling within the specific classes outlined above, including without limitation: surfactant adjuvants, sticker adjuvants, extender adjuvants, plant penetrant adjuvants, compatibility agent adjuvants, buffer adjuvants, pH modifier adjuvants, mineral control adjuvants, drift retard adjuvants, defoaming adjuvants, thickener adjuvants, oil-based adjuvants, special purpose adjuvants, utility adjuvants, solvent adjuvants, and fertilizer-based adjuvants.

According to the present invention, alkylene carbonates may be included in an agriculturally useful formulation which contains any number of pesticides, herbicides, or mixtures thereof, including, but not limited to, the isopropylamine salt, ammonium salt, or trimesium salt of glyphosate, the ammonium salt of glufosinate, paraquat (1,1'Dimethyl-4,4'bipyridinium dichloride), or diquat (1,1'-ethylene-2,2'-bipyridylium dibromide). However, the use of the adjuvants of the present invention with glyphosate is of particular interest because glyphosate is probably the most widely used herbicide.

Glyphosate, or N-phosphonomethylglycine, is a well-known, broad-spectrum herbicide that is useful on essentially all annual and perennial plants, including, grasses, broad-leaved weeds, and woody plants. Glyphosate promotes plant necrosis by inhibiting aromatic amino acid biosynthesis. By inhibiting aromatic amino acid synthesis, and thereby protein synthesis, glyphosate initially suppresses plant growth, which is soon followed by plant necrosis. In its free acid form, glyphosate has a low water solubility. As such, water-based glyphosate compositions typically contain a water-soluble salt of glyphosate, such as the isopropylamine salt, ammonium salt, or trimesium salt.

A herbicide composition according to the present invention comprises an agriculturally effective amount of a agriculturally-active material and one or more alkylene carbonates in addition to an adjuvant composition, which preferably comprises a surfactant. Preferably, the alkylene carbonate is present in an amount sufficient to enhance the effectiveness of the agriculturally-active material. A composition according to the present invention may optionally also comprise water or other formulation aids. Such formulation aids may include, but are not limited to, anti-freeze agents, dyes, thickening agents, anti-foaming agents, UV stabilizers, or pH adjusting agents. The relative amount of water or other formulation aids that may need to be blended in the herbicide composition will depend on a variety of factors, including the nature of the herbicide, the proposed mode of application of the final herbicide formulation, the nature of the vegetation to be treated, etc. Preferably, the alkylene carbonate component of the composition comprises a blend of propylene carbonate and butylene carbonate. The particular amount of propylene carbonate and butylene carbonate in the blend will depend on a variety of factors, including the nature of the surfactant composition, the nature of the agriculturally-active material used, the proposed mode of application, etc. The surfactant component of the composition may comprise any number of surfactants, including, but not limited to, nonionic surfactants, anionic surfactants, cationic surfactants, and amphoteric surfactants. Preferably, the surfactant component of the adjuvant composition is a nonionic surfactant. More preferably, the surfactant component of the adjuvant composition is an alkyl phenol ethoxylates or branched alcohol ethoxylates. According to one preferred form of the invention, the agriculturally-active material is a herbicide, which preferably comprises the isopropylamine salt, ammonium salt, or trimesium salt of glyphosate, the ammonium salt of glufosinate, paraquat (1,1'Dimethyl-4,4'bipyridinium dichloride), or diquat (1,1'-ethylene-2,2'-bipyridylium dibromide). The relative amount of the agriculturally-active material that should be blended with an adjuvant in a composition according to the invention will vary depending on a variety of factors, including the nature of the agriculturally-active material, the nature of the vegetation or pest to be treated, the method of application, whether the agriculturally-active material is to be formulated as a water-based or solid composition, etc. In any case, a composition according to the present invention should include an effective agriculture enhancing amount of a agriculturally-active material, and a sufficient amount of an adjuvant and an alkylene carbonate to enhance the effectiveness of the agriculturally-active material. As used herein, the term "effective agriculture enhancing amount" means the amount of herbicide necessary to promote plant necrosis in the case of plant life or the amount of pesticide necessary to negatively impact the longevity of a destructive insect species.

A composition according to the present invention may be prepared as either liquid or solid compositions. Liquid compositions may include solutions ready for immediate application, aqueous concentrates intended to be diluted with water before application, or microencapsulated actives suspended in liquid media. Solid compositions may include, but are not limited to, water dispersible granules, water soluble granules, microencapsulated actives, free-flowing particulate compositions, or granular-based solids that have been compressed into tablets or briquets of any desired size and shape. Optionally, solid compositions may include formulations where the composition is absorbed onto water-soluble or water insoluble inert dry carriers, including, but not limited to, MAGNESOL® carrier (commercially available from the Dallas Group of America, Inc., Whitehouse, N.J.).

A composition according to the present invention may be applied to vegetation as either a liquid or solid composition. Liquid herbicide compositions are typically sprayed on the vegetation to be treated, and typically comprise either liquid concentrates or dissolved or dispersed solid compositions. Liquid compositions may also be injected into, or painted on the trunk portion of the vegetation to be treated. Solid granular compositions may be spread on or around the vegetation to be treated.

The present invention further provides for adjuvant compositions that increase the bioefficacy of a herbicidal active ingredient. Such adjuvant compositions comprise one or more surfactants, one or more alkylene carbonates, and water. Such adjuvant compositions may optionally comprise one or more formulation aids. Such formulation aids may include, but are not limited to, anti-freeze agents, dyes, thickening agents, anti-foaming agents, UV stabilizers, or pH adjusting agents. Whether formulation aids should be added to an adjuvant composition will depend on a variety of factors, including the nature of the herbicide to be blended with the adjuvant composition, the proposed mode of application of the final herbicide formulation, the nature of the vegetation to be treated, etc.

The adjuvant compositions of the present invention may be blended with any number and/or mixtures of herbicides. Such herbicides may include, but are not limited to, the isopropylamine salt, ammonium salt, or trimesium salt of glyphosate, the ammonium salt of glufosinate, paraquat (1,1'Dimethyl-4,4'bipyridinium dichloride), or diquat (1,1'-ethylene-2,2'-bipyridylium dibromide). The relative amount of the adjuvant compositions of the present invention that should be blended with a herbicide will vary depending on a variety of factors, including the nature of the herbicide, the nature of the vegetation to be treated, the method of application, whether the herbicide is to be formulated as a water-based or solid composition, etc. In any case, the resulting herbicide formulation should include a herbicidally effective amount of a herbicidal active ingredient, and a sufficient amount of an adjuvant composition of the present invention to enhance the effectiveness of the herbicidal active ingredient.

The present invention further includes a process of killing or controlling weeds, insects, or unwanted vegetation comprising the step of applying an effective amount of a composition comprising: (a) a herbicidal or pesticidal active ingredient and (b) one or more alkylene carbonates and c) a surfactant to the foliage or tissue of the weeds, unwanted vegetation, or insects. The herbicidal active ingredient may comprise any number of herbicidal active ingredients, including, but not limited to, the isopropylamine salt, ammonium salt, or trimesium salt of glyphosate, the ammonium salt of glufosinate, paraquat (1,1'Dimethyl-4,4'bipyridinium dichloride), or diquat (1,1'-ethylene-2,2'-bipyridylium dibromide). Preferably, the alkylene carbonate component of the adjuvant composition comprises a blend of propylene carbonate and butylene carbonate. The particular amount of propylene carbonate and butylene carbonate in the blend will depend on a variety of factors, including the nature of the surfactant in the adjuvant composition, the nature of the herbicidal active ingredient used with the adjuvant composition, the proposed mode of application, etc. The surfactant component of the adjuvant composition may comprise any number of surfactants, including, but not limited to, nonionic surfactants anionic surfactants, cationic surfactants, and amphoteric surfactants. Preferably, the surfactant component of the adjuvant composition is a nonionic surfactant. More preferably, the surfactant component of the adjuvant composition is an alkyl phenol ethoxylates or branched alcohol ethoxylates. The herbicide composition may additionally comprise water or other formulation aids. Such formulation aids may include, but are not limited to, anti-freeze agents, dyes, thickening agents, anti-foaming agents, UV stabilizers, or pH adjusting agents. The relative amount of water or other formulation aids that may optionally be included in the herbicide composition will depend on a variety of factors, including the nature of the herbicidal active ingredient to be blended with the adjuvant composition, the proposed mode of application of the final herbicide formulation, the nature of the vegetation to be treated, etc.

It is understood that variations may be made in the foregoing without departing from the scope of the invention. For example, although the adjuvants and adjuvant compositions of the present invention are primarily discussed as being incorporated into water-based herbicide compositions, it is understood that the adjuvants and adjuvant compositions of the present invention may also be incorporated into dry granular herbicide formulations or solvent-based formulations. In addition, although the adjuvants and adjuvant compositions of the present invention are primarily discussed as being incorporated into glyphosate formulations, the adjuvants and adjuvant compositions of the present invention may be incorporated into any number of other herbicide formulations, including, but not limited to, macroemulsions, microemulsions, suspoemulsions, suspension concentrates, and other liquid and solid formulations known to those skilled in the art, to increase the bioefficacy of such herbicides.

The following examples are illustrative of the present invention, and are not intended to limit the scope of the invention in any way. All parts and percentages given herein are expressed on a weight basis, based upon the total weight of the composition specified, unless stated otherwise.

Phytotoxicity of PC and BC

EXAMPLE 1

The phytotoxicity of PC and BC was studied on soybeans (DeKalb CX242RR), corn (Pioneer 3757IR), and tomatoes (Roma Italian canner). A 75% PC/25% BC blend and a 25% PC/75% BC blend were applied at 0.5% in tap water at 10 gal/acre spray volume. The vegetation was sprayed at the five to six leaf stage, and evaluated three and seven days after treatment (DAT). There were four replicates per treatment. The alkylene carbonates showed no adverse effects on the vegetation. Even on very sensitive tomatoes, the alkylene carbonates proved to be completely phytobland, with absolutely no observed necrosis.

Bioefficacy Testing

EXAMPLE 2

The adjuvancy of alkylene carbonates with glyphosate was then tested. Bioefficacy testing was conducted on lambsquarters and velvetleaf weeds. The mono-isopropylamine salt of glyphosate was applied to velvetleaf and lambsquarters weeds at 0.25 lb ae/acre, and the adjuvant mixtures were present at 0.1 v/v%. The spray volume was 20 gal/acre, and application was made at 25 psig. There were four replicates per treatment, and the plants were observed for necrosis at seven, ten, and fourteen DAT. Table 3 shows the adjuvant mixtures that were evaluated.

TABLE 3

| Adjuvant Mixtures | | | | | | |
|---|---|---|---|---|---|---|
| | APE DEG | APE PC | APE BC | BAE DEG | BAE PC | BAE BC |
| SURFONIC ® N-95 APE[1] | 51.0 | 51.0 | 51.0 | — | — | — |
| SURFONIC ® DDA-8 BAE[2] | — | — | — | 51.0 | 51.0 | 51.0 |
| Diethylene Glycol (DEG) | 39.0 | — | — | 39.0 | — | — |
| 75% PC/25% BC | — | 39.0 | — | — | 39.0 | — |
| 25% PC/75% BC | — | — | 39.0 | — | — | 39.0 |
| Water | 10.0 | 10.0 | 10.0 | 10.0 | 10.0 | 10.0 |

[1]alkyl phenol ethoxylate (APE)
[2]branched alcohol ethoxylate (BAE)

Evaluations, with the same adjuvant mixtures listed above, were also made with ammonium sulfate (AMS) at 17 lb/100 gallons water carrier. For control purposes, a group of plants was not treated with any glyphosate, and another group of plants was treated with only glyphosate.

The two alkylene carbonate blends of PC and BC were compared to diethylene glycol (DEG) as a standard solvent in combination with two different nonionic surfactant systems. One surfactant system was a SURFONIC® N-95 alkyl phenol ethoxylate, and the second surfactant system was a SURFONIC® DDA-8 branched alcohol ethoxylate. (SURFONIC® brand ethoxylates are commercially available from Huntsman Petrochemical Corporation, Houston, Tex.).

The results of the bioefficacy testing are summarized in FIGS. 1-4. The results are expressed in terms of percent control, where 0% represents no plant necrosis, and 100% represents complete plant necrosis.

Figure 1:
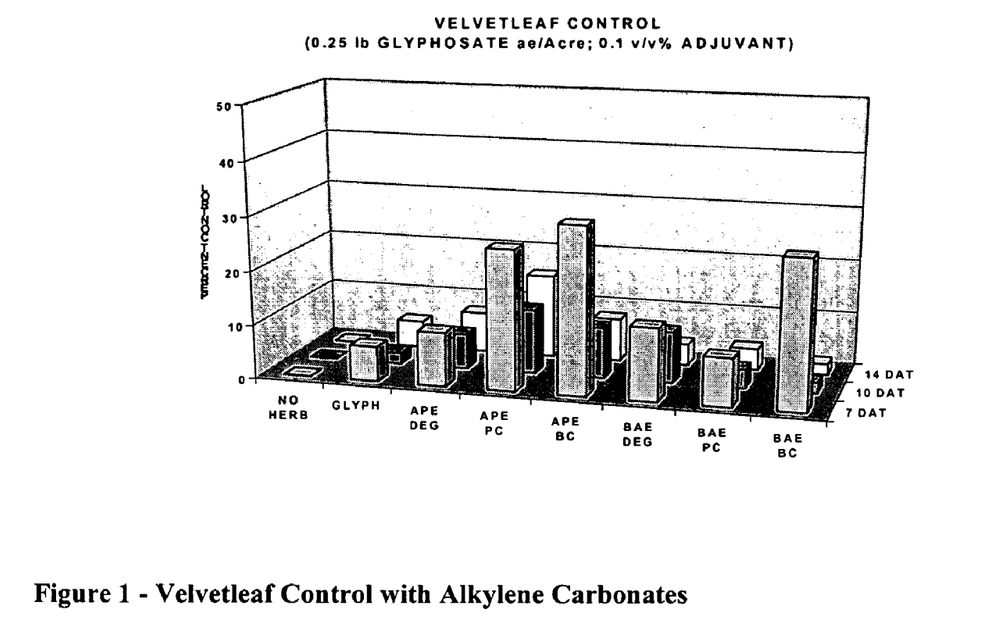
FIG. 1 shows the effect of alkylene carbonate on glyphosate efficacy with respect to velvetleaf control.

FIG. 1 shows the results of velvetleaf control using glyphosate in combination with alkylene carbonate mixtures used as spray tank adjuvants. FIG. 1 shows that there is very little observed necrosis with glyphosate alone. Adding APE and DEG raised initial kill marginally. Adding PC and BC with APE dramatically improved initial kill at 7 DAT, with PC providing the greatest long-term kill at 14 DAT. With the BAE, similar performance was seen with BC, but PC did not perform better than DEG.

Figure 2:
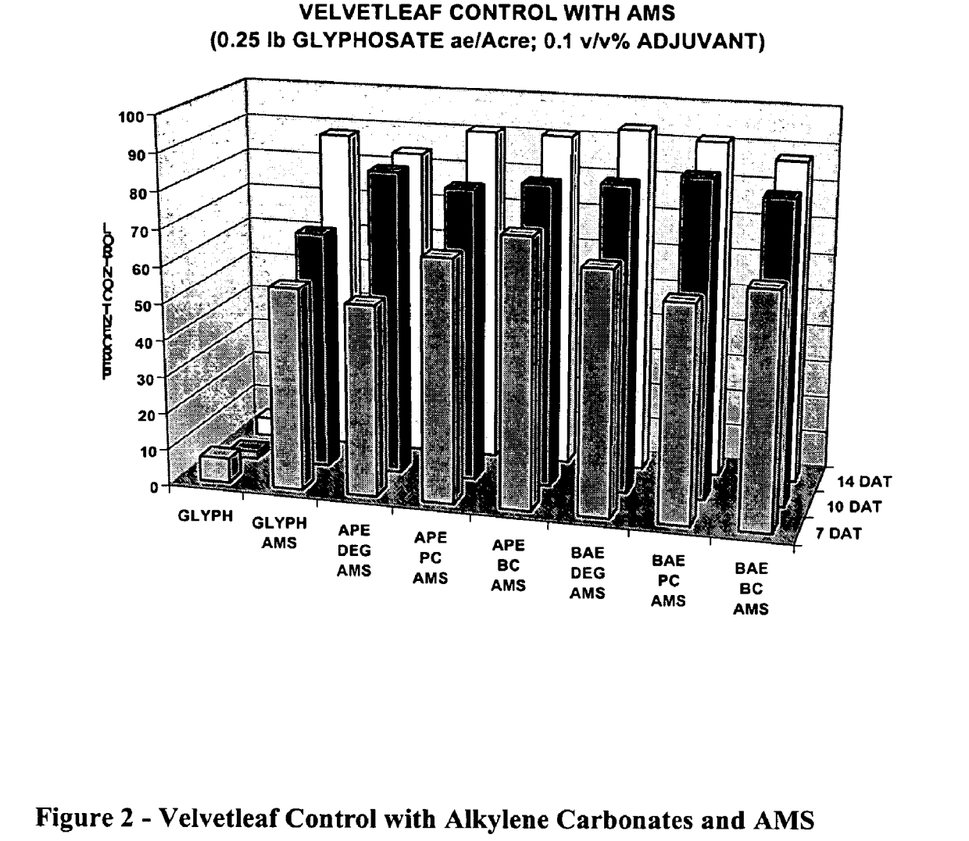
FIG. 2 shows the effect of alkylene carbonate on glyphosate efficacy with respect to velvetleaf control in a formulation containing AMS.

FIG. 2 shows that the addition of AMS to the spray solution dramatically increases velvetleaf necrosis. There is still the 7 DAT trend with APE where PC and BC improve initial kill over DEG or no surfactant. By 14 DAT, all systems studied achieved almost complete weed kill.

Figure 3:
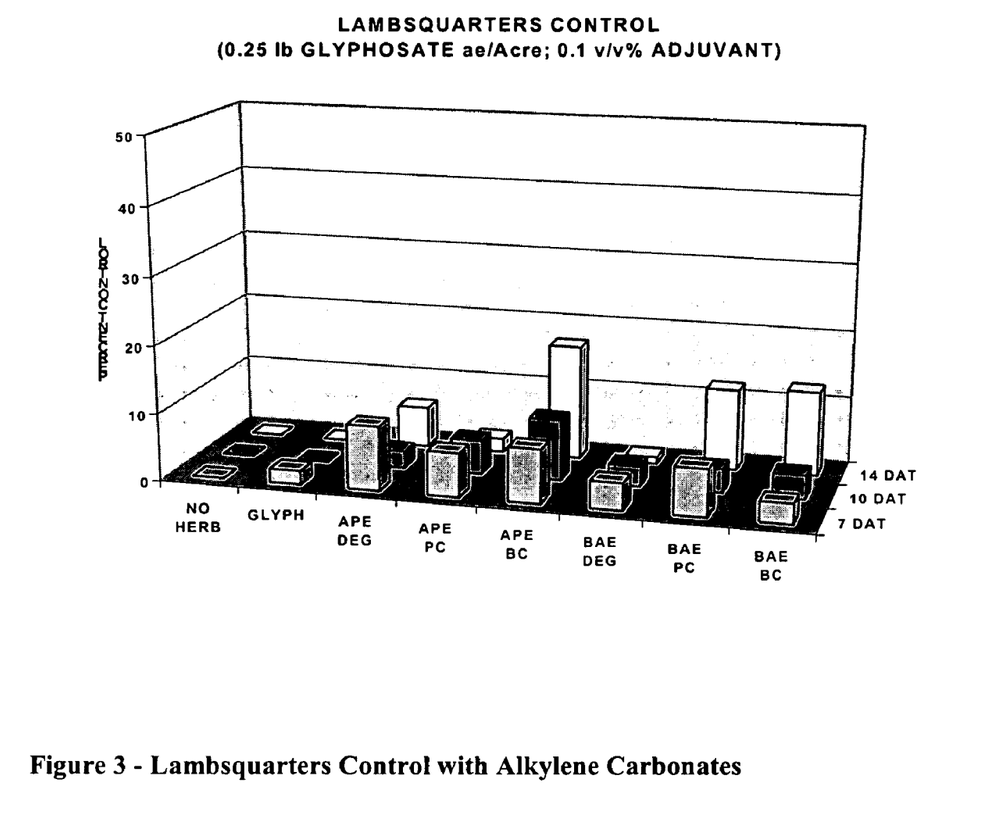
FIG. 3 shows the effect of alkylene carbonate on glyphosate efficacy with respect to lambsquarters control.

FIG. 3 shows the results of lambsquarters control using glyphosate in combination with alkylene carbonate spray tank adjuvants. Again, there is very little observed necrosis with glyphosate alone. Adding APE and DEG improves kill marginally. The addition of PC improves initial kill with both APE and BAE surfactants, but the sustained kill is better with BAE. BC improves both initial and sustained kill with APE and BAE.

Figure 4:
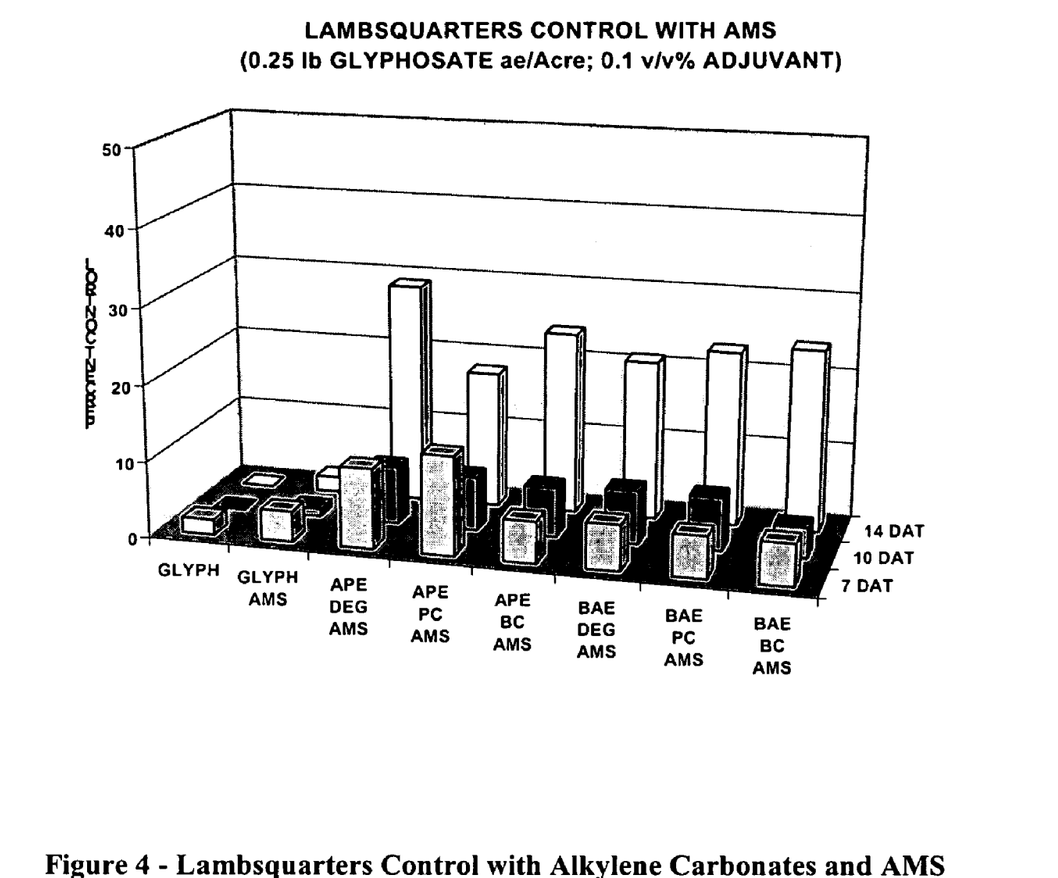
FIG. 4 shows the effect of alkylene carbonate on glyphosate efficacy with respect to lambsquarters control in a formulation containing AMS.

FIG. 4 shows the results of lambsquarters control using glyphosate in combination with alkylene carbonates and AMS. Adding AMS alone does not produce the dramatic improved efficacy as seen with velvetleaf. Adding surfactant and solvent to the tank mix does improve sustained kill dramatically.

The results of the bioefficacy testing show that alkylene carbonates should make ideal tank mix adjuvants. The alkylene carbonates improve initial kill when used in conjunction with glyphosate.

Alkylene carbonates useful as components of a composition according to the invention may be represented by the general structure:

in which each of $R_1$ and $R_2$ may be independently a hydrogen, hydroxymethyl, $C_1$ though $C_{18}$ alkyl, including straight chain or branched alkyls. R1 and R2 may also comprise aryl or alkylaryl groups, in which the benzene ring is substituted or unsubstituted with $C_1$ though $C_{18}$ alkyl groups. As but a few examples, when $R_1$ is hydroxymethyl and $R_2$ is hydrogen, then the structure represents glycerine carbonate (4-hydroxymethyl-1,3-dioxolan-2-one); when $R_1$ and $R_2$ are both hydrogen, the structure represents ethylene carbonate; when $R_1$ is hydrogen and $R_2$ is a methyl group, the structure represents propylene carbonate; and when $R_1$ is hydrogen and $R_2$ is an ethyl group, the structure represents butylene carbonate.

According to one preferred form of the invention, the alkylene carbonate is present in any amount between about 3% and 75% by weight based upon the total weight of said composition. According to another form of the invention, the alkylene carbonate is present in any amount between about 6% and 40% by weight based upon the total weight of said composition. In another form of the invention, the alkylene carbonate is present in any amount between about 8% and 35% by weight based upon the total weight of said composition. In another form of the invention, the alkylene carbonate is present in any amount between about 10% and 20% by weight based upon the total weight of said composition. In another form of the invention, the alkylene carbonate is present in any amount between about 20% and 35% by weight based upon the total weight of said composition. In another form of the invention, the alkylene carbonate is present in any amount between about 50% and 75% by weight based upon the total weight of said composition. In another embodiment, all features are as herein described, except the alkylene carbonate is present in an effective efficacy-enhancing amount with respect to one or more active ingredients present in the composition according to the invention.

Although illustrative embodiments have been shown and described, a wide range of modification, changes, and substitution is contemplated in the foregoing disclosure. In some instances, some features of the disclosed embodiments may be employed without a corresponding use of the other features. Accordingly, it is appropriate that the appended claims be construed broadly and in a manner consistent with the scope of the invention.

What is claimed is:

1. A composition useful in commercial agriculture comprising:
   a. a mixture of propylene carbonate and butylene carbonate;
   b. one or more water-soluble salt of glyphosate; and
   c. an agricultural adjuvant,
wherein the mixture is present in any amount between about 3% and 75% by weight based upon the total weight of said composition and wherein the mixture contains a ratio of propylene carbonate to butylene carbonate of from about 3:1 to about 1:3.

2. A composition according to claim 1 wherein said agricultural adjuvant is a surfactant.

3. A composition according to claim 2 wherein the surfactant is selected from the group consisting of: alkylphenol ethoxylates and branched alcohol ethoxylates.

4. A composition according to claim 1 further comprising water in an amount of at least 10.00% by weight based upon the total weight of said composition.

5. A composition of matter according to claim 1 wherein said adjuvant is a solvent adjuvant.

6. A composition according to claim 5 wherein said solvent is selected from the group consisting of: aromatic solvents, polycyclic aromatic solvents, aliphatic solvents, mineral oils vegetable oils, alkylester solvents, mineral spirits, petroleum distillates, acetate esters, crop oils, chlorinated hydrocarbons, naphthas, N-alkylpyrollidones, paraffinic solvents, seed oils, alkylated seed oils, citrus oils and alcohols.

7. A composition according to claim 1 wherein said adjuvant is an adjuvant selected from the group consisting of: ammonium nitrate, ammonium sulfate, and urea ammonium nitrate.

8. In a composition of matter useful for controlling the proliferation of insects or foliage which contains a water-soluble salt of glyphosate, and which is intended to be applied to crops, foliage, or soil, the improvement comprising: the inclusion of a mixture of propylene carbonate and butylene carbonate in a ratio of from about 3:1 to about 1:3, in said composition of matter.

9. A process for controlling unwanted foliage or insects comprising the step of applying an effective pesticidal amount of a composition according to claim 1 to foliage.

10. A process for controlling unwanted foliage or insects comprising the step of applying an effective pesticidal amount of a composition according to claim 8 to foliage.

* * * * *